(12) United States Patent
Purohit et al.

(10) Patent No.: US 11,285,152 B2
(45) Date of Patent: Mar. 29, 2022

(54) STABLE ORAL PHARMACEUTICAL COMPOSITION OF IMATINIB

(71) Applicant: KASHIV BIOSCIENCES, LLC, Piscataway, NJ (US)

(72) Inventors: Parva Yogeshchandra Purohit, Ahmedabad (IN); Paras Rasiklal Vasanani, Ahmedabad (IN); Vikas Maheshbhai Agrawal, Ahmedabad (IN); Kiran Dilipbhai Patel, Des Plaines, IL (US)

(73) Assignee: KASHIV BIOSCIENCES, LLC, Piscataway, NJ (US)

( * ) Notice: Subject to any disclaimer, the term of this patent is extended or adjusted under 35 U.S.C. 154(b) by 45 days.

(21) Appl. No.: 16/631,933

(22) PCT Filed: Jul. 16, 2018

(86) PCT No.: PCT/IB2018/055245
§ 371 (c)(1),
(2) Date: Jan. 17, 2020

(87) PCT Pub. No.: WO2019/016673
PCT Pub. Date: Jan. 24, 2019

(65) Prior Publication Data
US 2020/0222402 A1   Jul. 16, 2020

(30) Foreign Application Priority Data
Jul. 20, 2017 (IN) .............................. 201721025890

(51) Int. Cl.
| A61K 31/506 | (2006.01) |
| A61K 9/00 | (2006.01) |
| A61K 9/20 | (2006.01) |

(52) U.S. Cl.
CPC .......... *A61K 31/506* (2013.01); *A61K 9/0053* (2013.01); *A61K 9/2095* (2013.01)

(58) Field of Classification Search
CPC .................................................. A61K 31/506
See application file for complete search history.

(56) References Cited

U.S. PATENT DOCUMENTS

| 3,518,343 A | 6/1970 | Welsh |
| 5,521,184 A | 5/1996 | Zimmermann |
| 6,958,335 B2 | 10/2005 | Buchdunger et al. |
| 8,414,918 B2 * | 4/2013 | Gerber .................... A61P 11/00 424/464 |
| 9,011,911 B2 * | 4/2015 | Luftensteiner ....... A61K 9/2009 424/464 |
| 9,198,862 B2 | 12/2015 | Pilgaonkar et al. |
| 9,750,700 B2 | 9/2017 | Adibhatla et al. |
| 2006/0275372 A1 | 12/2006 | Jenkins et al. |
| 2013/0085145 A1 * | 4/2013 | Prasad ................. A61K 9/2027 514/252.18 |

FOREIGN PATENT DOCUMENTS

| EP | 1762230 | 8/2006 |
| EP | 2782560 | 10/2014 |
| WO | WO200057857 | 10/2000 |
| WO | WO2003090720 | 11/2003 |
| WO | WO2011160798 | 12/2011 |
| WO | WO2017078647 | 5/2017 |

OTHER PUBLICATIONS

Siden et al.,"Disintegration of chemotherapy tablets for oral adminislialion in patients with swallowing difficulties," Journal of oncology pharmacy practice, 19(2)(2013) ; 145-146.
Heim et al., "G-CSF for Imatinib-lnduced Neutropenia,"Leukemia (2003)17, 805-807.

* cited by examiner

*Primary Examiner* — Rei Tsang Shiao
(74) *Attorney, Agent, or Firm* — Pergament & Cepeda LLP; Milagros A. Cepeda; Edward D. Pergament

(57) ABSTRACT

The present invention relates to a stable orally disintegrating pharmaceutical formulation comprising imatinib or a pharmaceutically acceptable salt thereof and a one or more pharmaceutically acceptable excipients. The present invention further relates to a stable dispersible pharmaceutical formulation comprising imatinib or a pharmaceutically acceptable salt thereof, and a one or more pharmaceutically acceptable excipients. Moreover, the present invention also relates to a novel pharmaceutical sachet formulation comprising an effective amount of imatinib or a pharmaceutically acceptable salt thereof, a flavouring agent, a sweetener and a one or more pharmaceutically acceptable excipients.

20 Claims, No Drawings

STABLE ORAL PHARMACEUTICAL COMPOSITION OF IMATINIB

RELATED APPLICATIONS

This application is a U.S. National Stage Patent Application under 35 U.S.C. § 371 of International Application No. PCT/IB2018/055245, filed on Jul. 16, 2018, which claims priority to IN Provisional Patent Application No. IN201721025890, filed Jul. 20, 2017, the disclosure of which is hereby incorporated by reference in its entirety

TECHNICAL FIELD

The present invention relates to a stable orally disintegrating pharmaceutical formulation comprising imatinib or a pharmaceutically acceptable salt thereof and a one or more pharmaceutically acceptable excipients. The present invention further relates to a stable dispersible pharmaceutical formulation comprising imatinib or a pharmaceutically acceptable salt thereof, and a one or more pharmaceutically acceptable excipients. Moreover, the present invention also relates to a novel pharmaceutical sachet formulation comprising imatinib or a pharmaceutically acceptable salt thereof, and a one or more pharmaceutically acceptable excipients.

BACKGROUND ART

Imatinib is a protein-tyrosine kinase inhibitor. Chemically, it is known as 4-(4-methylpiperazin-1-ylmethyl)-N-[4-methyl-3-[(4-pyrinin-3-yl) pyrimidin-2-ylamino] phenyl] benzamide mesylate, and has the following chemical structure.

Formula I

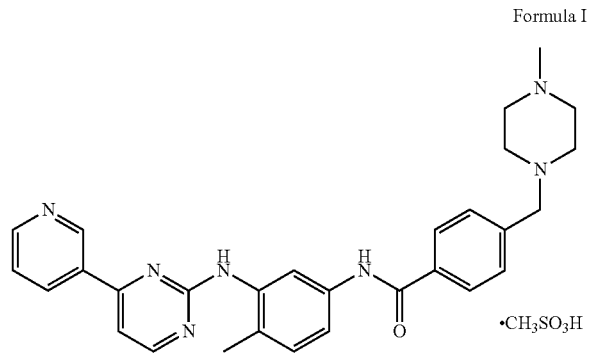

Imatinib mesylate is a white to off white to brownish or yellow tinged crystalline powder with an unpleasant, bitter or otherwise disagreeable taste when administered orally. Imatinib mesylate is soluble in aqueous buffers <pH 5.5, but is very slightly soluble to in soluble in neutral/alkaline aqueous buffers. In non-aqueous solvents, the drug substance is freely soluble to very slightly soluble in dimethyl sulfoxide, methanol and ethanol, but is insoluble in n-octanol, acetone and acetonitrile. Imatinib is usually administered orally in the form of a suitable salt, e.g., in the form of imatinib mesylate.

Currently, Imatinib is marketed under brand name of Gleevec by Novartis Pharmaceuticals in Oral Tablets dosage form of strengths of 100 mg & 400 mg for the treatment of chronic myeloid leukemia (CML) and gastrointestinal tract cancers (GIST).

U.S. Pat. No. 5,521,184 discloses the imatinib or the pharmaceutically acceptable salts thereof. Example 21 is imatinib mesylate and its crystalline forms are disclosed in the international patent application numbered WO 1999/03854 as well as U.S. Pat. No. 6,958,335 discloses imatinib use in the treatment of gastrointestinal stromal tumours (GIST).

WO 2003/090720 discloses conventional tablets with high drug loading content comprising a pharmacologically effective amount of imatinib or pharmaceutically acceptable salt thereof present in an amount of from about 30% to 80% in weight of the active moiety based on the total weight of the tablet.

The approved Gleevec label dosage and administration discloses that for patients who are unable to swallow the film-coated tablets, the tablets may be dispersed in a glass of water or apple juice. The required number of tablets should be placed in the appropriate volume of beverage (approximately 50 mL for a 100 mg tablet, and 200 mL for a 400 mg tablet) and stirred with a spoon. The suspension should be administered immediately after complete disintegration of the tablet(s).

The hospital publication from University of Wisconsin & University of Michigan (J. Oncology Pharm Practice; 19(2); page 145-150; by Rivka Siden & M. Wolf; Page) discloses an oral syringe administration of oral chemotherapeutic tablets for evaluating the feasibility of disintegration. It specifically discloses that administration of oral chemotherapeutic drugs can be problematic in patients with swallowing difficulties and patients having an inability to swallow solid dosage forms can compromise compliance and may lead to poor clinical outcome. Further, the current technique of tablet crushing to aid in administration is considered an unsafe practice and may lead to poor clinical outcome. The publication further discloses that recently, manufacturers started to include information on dispersing drugs in liquid just prior to administration for newer chemotherapeutic drugs. For example, the package insert of imatinib indicates that one 400 mg tablet may be dispersed in 200 mL of water or juice prior to administration. However, this large volume may not be suitable for small children or patients with swallowing difficulties.

Further, it is known that patients who are unable to swallow tablets (geriatric or pediatric or adults patients with swallowing difficulties) then they generally prefer to crush it and swallow with water, which further increase the rate of medication errors in dosing specifically in children who received chemotherapy at home. It is reported that a medication error occurred for almost 10% of chemotherapy agents prescribed in these patients.

The scientific studies published by University Hospital Basel from D. Heim et al. (Leukemia (2003) 17, 805-807, D. Helm et al) disclose imatinib induces neutropenia in patients. It mentions that depending on the disease stage, up to 70% of the patients experience an NCI grade 3 or 4 neutropenia or thrombocytopenia during imatinib therapy. Further, the publicly available literatures of neutropenia disclose that the neutropenia results in various types of infections in patients including otis media; tonsillitis (painful swallowing); sore throat; mouth ulcers; gum infection. This creates difficulties in swallowing in patients with conventional tablet administration.

EP 2782560 A1 patent application discloses a pharmaceutical powder formulation comprising enteric coated granules of imatinib which is reconstituted with diluent before use.

The IN1314/CHE/2011 patent application discloses taste masked orally disintegrating composition by use of taste masking polymer, which need to be coated on imatinib containing core.

From the above prior arts and publicly available literatures, it is observed that commercially available Gleevec tablet formulations poses difficulties in swallowing of tablets in patients due to pain while swallowing, age, symptoms of the disease as well as adverse effects resulting from the treatments and psychological causes. Further, crushing of formulation also leads to medication error in patients in such a life threating cancers disease condition. Hence, it always remains challenge for industry to increase patient's compliance and provide exact required dose of drug in such diseased conditions and it is an unmet need of society based on looking at currently administration practices adopted by hospitals.

In the present invention, the inventors have discovered a novel approach for solving above problems by developing easy to swallow, stable pharmaceutical compositions such as orally disintegrating tablet, orally disintegrating film, dispersible tablet and sachet formulations of imatinib which provides better patient compliance in cancerous patients by various means like ease of dose administration, do not causes difficulties in swallowing available tablet formulation and avoids medication errors.

Further, the present invention compositions remain stable for a long period of time without compromising the therapeutic efficacy and increases patients compliance.

SUMMARY OF INVENTION

The present invention relates to a stable orally disintegrating pharmaceutical formulation comprising imatinib or a pharmaceutically acceptable salt thereof, and a one or more pharmaceutically acceptable excipients.

Further, the present invention relates to a stable pharmaceutical dispersible formulation of imatinib or a pharmaceutically acceptable salt thereof, and a one or more pharmaceutically acceptable excipients.

Moreover, the present invention relates a novel pharmaceutical sachet formulation comprising imatinib or a pharmaceutically acceptable salt thereof, and a one or more pharmaceutically acceptable excipients.

Further, the present invention relates to a process of preparing a stable orally disintegrating or dispersible or sachet pharmaceutical formulation comprising imatinib or a pharmaceutically acceptable salt thereof and a one or more pharmaceutically acceptable excipients.

DETAILED DESCRIPTION

The present invention relates to a stable oral pharmaceutical formulation comprising imatinib or a pharmaceutically acceptable salt thereof and a process for preparing the pharmaceutical composition.

Specifically, the present invention relates to a stable orally disintegrating pharmaceutical formulation comprising imatinib or a pharmaceutically acceptable salt thereof, and a one or more pharmaceutically acceptable excipients.

The term "Imatinib" includes the compound imatinib, pharmaceutically acceptable salts, esters and prodrugs thereof, the active metabolites of imatinib, and any of their polymorphs, solvates, hydrates, and combinations thereof such as hydrated salts of imatinib.

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. The pharmaceutically acceptable salts include acid salt like mineral acid salt, such as a hydrochloride hydrobromide, sulfate, etc., organic acid salt such as a succinate, maleate, fumarate, malate, tartrate, etc., sulfonate salt such as a methanesulfonate (mesylate), benzenesulfonate, toluenesulfonate, etc, basic salts like alkali metal salt such as a sodium salt, potassium salt, and alkaline earth metal salt, such as a calcium salt, etc.

The terms "orally disintegrating" refer to a solid dosage form which disintegrates rapidly in the oral cavity of a patient, without chewing. The rate of disintegration can vary, but it is faster than the rate of disintegration of conventional solid oral dosage forms which are intended to be swallowed immediately after administration. The orally disintegrating formulation is disintegrated in less than 1 minute, preferably in less than 30 seconds as per USP disintegration test described in USP 24-NF 19 or an equivalent alternative test.

The term "dispersible tablet" refers to a tablet, which may dispersed in water before administration, providing a homogeneous dispersion and remains stable for an adequate period of time.

The term "homogeneous dispersion" means that the dispersion produced upon contact with water which ensures the uniformity of pharmacologically active ingredient content for a reasonable period of time.

The term "sedimentation rate" means the rate at which the pharmacologically active ingredients settle from the dispersion.

The term "about" refers to any value which lies within the defined range by present inventors from a variation of up to ±10% of the claimed value.

The term "stable" means a drug substance and/or pharmaceutical composition for pharmaceutical use which remains stable as per ICH guidelines.

The term "ICH guidelines" means composition remains stable for longer period of time at 25° C./60%+5% RH, 30° C./65%+5% RH, and 40° C./75%+5% RH conditions for a time period of at least 6 months.

A first aspect of the present invention relates to a pharmaceutical composition comprising imatinib or a pharmaceutically acceptable salt thereof, a one or more pharmaceutically acceptable excipients, and super disintegrants. The present invention addresses the problems associated with the commercially available Gleevec tablet formulation which poses difficulties in swallowing of tablets in patients due to psychological causes, age, symptoms of the disease as well as adverse effects resulting from the treatments. Further, crushing of formulation also leads to medication error in patients in such a life threating cancers disease condition.

Hence, the present invention has found a novel approach for solving this problem by developing stable orally disintegrating pharmaceutical formulations of imatinib which increase patient's compliance in cancerous patients by various means like ease of dose administration, do not causes difficulties in swallowing tablets formulations as well as also acceptable from drug property aspect.

The orally disintegrating compositions of the present invention are palatable with good disintegration characteristics and pharmacokinetics property, which provide greater compliance to patients who have difficulty in swallowing conventional imatinib tablets.

Further, it is difficult to develop orally disintegrating formulations because of several different reasons and requirements such as stability and solubility besides suitable disintegration time of formulations to achieve rapid disintegration.

According to one embodiment of the present invention, there is provided a stable orally disintegrating pharmaceutical formulation comprising imatinib or a pharmaceutically acceptable salt thereof, a super-disintegrants and a one or more pharmaceutically acceptable excipients.

According to other embodiment of the present invention, there is provided a stable pharmaceutical dispersible formulation of imatinib or a pharmaceutically acceptable salt thereof, and a one or more pharmaceutically acceptable excipients.

According to other embodiment of the present invention, there is provided a stable dispersible pharmaceutical formulation of imatinib or a pharmaceutically acceptable salt thereof, at least one excipient which reduces the sedimentation rate of imatinib and a one or more pharmaceutically acceptable excipients.

The dispersible tablet of the present invention rapidly disperses in water to produce a homogeneous dispersion that ensures uniformity of dose and desired therapeutic outcome. The present invention particularly relates to the selective use of excipients that reduce the sedimentation rate by reducing the surface tension between the aqueous media and the insoluble active, thereby facilitating the active's maintenance in the aqueous media.

According to another embodiment of the present invention, there is provided a pharmaceutical sachet formulation comprising an effective amount of imatinib or a pharmaceutically acceptable salt thereof and a one or more pharmaceutically acceptable excipients.

According to another embodiment of the present invention, there is provided a pharmaceutical sachet formulation comprising an effective amount of imatinib or a pharmaceutically acceptable salt thereof, a flavouring agent, a sweetener and a one or more pharmaceutically acceptable excipients.

The present invention covers aspects for a sachet formulation which is reconstituted with a diluent just before use. The sachet formulation of present invention may be introduced by a patient into a suitable amount of liquid, preferably water, as imatinib is very soluble in water to form a therapeutic formulation in situ, and the therapeutic formulation is then taken by the patient. The resulting mixture has a pleasant mouth-feel and therefore can be conveniently administered to a patient as a drink. The drink can be a suspension or solution. Alternatively, the sachet formulations of the invention may be administered by a patient directly or as a mixture with foods, such as mashed potatoes or oatmeal or with juice. This also affects the psychological state of the patient positively and also has higher compliance to the treatment and therefore, the treatment's success rate will increase.

According to another embodiment of the present invention, there is provided a pharmaceutical composition of imatinib or a pharmaceutically acceptable salt thereof and one or more pharmaceutically acceptable excipients selected from diluents, binders, super-disintegrants, polymers, lubricants, glidants, sweeteners, flavouring agents, sedimentation rate reducing agents (such as polymers, wetting agents etc.), taste-masking agents, coating agents, solvents and mixtures thereof.

According to another embodiment of the present invention, there is provided a pharmaceutical composition of imatinib or a pharmaceutically acceptable salt thereof, wherein the imatinib or pharmaceutically acceptable salt thereof may present in amount from about 50 mg to about 800 mg, preferably from about 100 mg to about 400 mg, more preferably from 100 mg or 400 mg of imatinib, preferably imatinib mesylate.

The diluents used in the pharmaceutical composition of the present invention are selected from the group consisting of a lactose, microcrystalline cellulose, starch, pre-gelatinized starch, calcium phosphate, calcium sulfate, calcium carbonate, mannitol, sorbitol, xylitol, sucrose, maltose, fructose, dextrose, maltodextrin, dextrates, dextrin, and the like thereof. The diluents may present in an amount from about 1% to 80% by weight of the composition, preferably from about 10% to 70% by weight of composition.

The binders used in the pharmaceutical composition of the present invention are selected from the group consisting of a starches, natural and synthetic gums, cellulose derivatives, gelatin, povidone, copovidone, polyethylene glycol, waxes, sodium alginate, alcohols, water, and the like thereof. The binders may present in an amount from about 0.01% to 20% by weight of composition, preferably from about 3% to 15% by weight of composition, and more preferably from about 5 to 10% by weight of composition.

The term "super disintegrants" referred as a substance which facilitates rapid disintegration of the present oral dosage forms following introduction into the oral cavity. The super disintegrants used in the pharmaceutical composition of the present invention are selected from the group consisting of a cross-linked polymer such as crospovidone (crosslinked PVP), modified starches such as sodium starch glycolate, cross-linked cellulose such as crosslinked sodium carboxymethyl cellulose (croscarmellose sodium), low substituted hydroxypropyl cellulose, cross-linked alginic acid, natural polymer such as soy polysaccharides, ion-exchange resins, calcium silicate and mixtures thereof. According to the present invention, preferable disintegrants are crospovidone, croscarmellose sodium and sodium starch glycolate. The disintegrants may present in an amount from about 1% to 30% by weight of composition, preferably from about 1% to 25% by weight of composition, and more preferably employed in an amount in a range of from about 5% to 20% by weight of composition.

According to another aspect of the present invention, there is provided a formulation comprising a solid dispersion or intimate mixture of a poorly water soluble drug and a polymer, wherein said polymers are selected from the group consisting of hypromellose, copovidone, povidone, methyl cellulose, hydroxyethyl cellulose, hydroxypropyl cellulose, ethylcellulose, pyroxylin, polyethylene oxide, polyvinyl alcohol, polyethylene glycol, and polyvinyl caprolactam-polyvinyl acetate-polyethylene glycol, polysaccharides, polypeptides, and methacrylic acid copolymers, ethyl acrylic acid copolymers. A preferred polymer is acrylic products such as poly(meth)acrylate (EUDRAGIT™) copolymers are available in various physical forms, for example, EUDRAGIT EPO being a powder form of EUDRAGIT E 100. The polymers may present in an amount from about 1 to about 60 wt. %, by weight of composition, preferably from about 5 to about 45 wt. %, and is more preferably employed in an amount in a range of from about 10 to about 30 wt. %.

The lubricants used in the pharmaceutical composition of the present invention are selected from the group consisting of a calcium stearate, Glyceryl monostearate, Glyceryl palmitostearate, hydrogenated castor oil, hydrogenated vegetable oil, light mineral oil, magnesium stearate, mineral oil, polyethylene glycol, stearic acid, zinc stearate, and sodium stearyl fumarate and a combination thereof. A preferred lubricant is magnesium stearate and sodium stearyl fumarate and may present in amount from about 0.1% to 10% by weight of composition, preferably from about 0.5 to 5% and more preferably from about 1% to 2% by weight of composition.

The glidants used in the pharmaceutical composition of the present invention are selected from the group consisting of a starch, talc, lactose, stearates, dibasic calcium phosphate, magnesium carbonate, magnesium oxide, calcium silicate, and colloidal silicon dioxide (Aerosil) and the like thereof. The Glidants may present in an amount from about 0.1% to 20% by weight of composition, preferably from about with amounts of about 0.5% to about 5%.

The sweeteners used in the pharmaceutical composition of the present invention are selected from the group consisting of a alitame, acesulfame potassium, aspartame, D-tryptophan, dextrose, erythritol, fructose, galactose, glycerol, glycyrrhizin, glucose, isomalt, xylitol, xylose, lactitol, lactose, levulose, maltitol, maltodextrin, maltol, maltose, corn syrup, neohesperidin dihydrochalcone, neotame, sodium saccharin, siclamate, sorbitol, sucralose, sucrose, tagatose, taumatin, trehalose, and the like thereof. The sweeteners may present in an amount about 25% or less by weight of composition, preferably from about 10% or less by weight of composition.

The flavouring agents used in the pharmaceutical composition of the present invention are selected from the group consisting of a natural flavoring oils, anethole, acetic acid, ascorbic acid, phosphoric acid, fumaric acid, lactic acid, lemon, linalool, malic acid, menthol, eucalyptol, orange, citric acid, cinnamone, tartaric acid, thymol, vanilla, strawberry, cherry Flavor (spray dried naturaltype), chocolate aroma or peppermint aroma and the like thereof. The flavouring agents may present in an amount less than about 10 wt % or less by weight of composition, preferably less than about 5.0 wt % or more preferably less than about 1.0 wt %.

The excipients used in the pharmaceutical composition of the present invention, which reduce the sedimentation rate of the active ingredient may include polymers, waxes, wetting agents or a like thereof. The wetting agent acts by reducing the surface tension between the aqueous media and the insoluble active, thereby facilitating the active's maintenance in the aqueous media.

The preferred excipients for reducing sedimentation rate are hydrophilic polymers. They increase the viscosity of the medium and maintain the wetted particles of the active substance(s) in homogeneous suspension, leading to reduction in their sedimentation rate. The preferred hydrophilic polymers are polyethylene oxide, hydroxypropyl cellulose, hydroxypropyl methylcellulose, hydroxyethyl cellulose, sodium carboxy methylcellulose, microcrystalline cellulose, guar gum, xanthan gum, alginates and combinations thereof. The hydrophilic polymer may present in an amount from about 1% to 75% by weight of composition, preferably from about 10% to 70% by weight of composition, and most preferably from about 5% to 50% by weight of composition.

The wetting agents used in the pharmaceutical composition of the present invention are selected from the surfactants, including nonionic, cationic, anionic, and zwitterionic type surfactants. These include sorbitan fatty acid esters, polyoxyethylene sorbitan fatty acid esters (Tween®), polyoxyethylene fatty acid esters, polyoxyethylene-polyoxypropylene copolymers and block copolymers and the like thereof. The wetting agents may present in an amount in a range of from about 1 to about 60 wt. %, by weight of composition, preferably from about 10 to about 40 wt. %, and is more preferably employed in an amount in a range of from about 20 to about 30 wt. %.

According to another embodiment, the orally disintegration formulations disintegrate in the oral cavity of a patients about 60 seconds or less, about 50 seconds or less, about 40 seconds or less, about 30 seconds or less, about 20 seconds or less, or about 10 seconds or less. Disintegration time in the mouth can be measured by observing the dissolution time of the tablet in purified water at about 37° C. using the USP basket-rack assembly method.

The composition of the present invention may be in the form of tablets, dispersible tablets, granules, pellets, minitablets, sachets, chewable tablets, powder for solution, powder for reconstitution, orally disintegrating films, wafers, or a like thereof which can be easily disintegrate in oral cavity after administration or dispersed/reconstituted in a suitable medium during administration.

In another embodiment, the compositions of the present invention can comprise imatinib particles (e.g., crystals), coated with a taste-masking layer to improve palatability of the composition. The taste-masking layer can be applied to the imatinib particles by any suitable method, for example microencapsulation, coacervation phase separation or fluidized bed coating methods.

The imatinib particles can be taste-masked with water-insoluble/water soluble polymers. Non-limiting examples of suitable water-insoluble polymers for the taste-masking layer include ethylcellulose, polyvinyl acetate (PVA), cellulose acetate (CA), cellulose acetate butyrate (CAB), methacrylate copolymers, such as those available under the tradename "EUDRAGIT" (e.g., type RL, RS, and NE30D), and combinations thereof. Non-limiting examples of water-soluble polymer include, e.g. sodium chloride, sucrose, povidone, and mixtures thereof.

The pharmaceutical composition of the present invention may further be film-coated using techniques well known in the art such as spray coating in a conventional coating pan or a fluidized bed processor or dip coating. Alternatively, coating may also be performed using the hot melt technique. The film coat comprises film-forming polymers, one or more pharmaceutically acceptable excipients and pharmaceutically acceptable solvents.

The pharmaceutical composition of the present invention can be obtained by a known conventional methods like dry granulation, wet granulation, direct compression, roller compaction, fluidized bed granulation, rapid mixture granulation, spray drying, freeze drying, solvent evaporation, hot-melt extrusion, extrusion spheronization, melt granulation or a like that.

According to another embodiment of the present invention, there is provided an orally disintegrating pharmaceutical composition comprising from about 1% to about 80% w/w of imatinib or a pharmaceutically acceptable salt thereof, from about 1% to about 80% w/w fillers, from about 0% to about 20% w/w of binders, from about 1% to about 30% w/w of disintegrants, from about 0% to about 60% w/w of polymers, from about 0.1% to about 10% w/w of lubricants, from about 0% to about 20% w/w of glidants, an amount about 25 wt % or less of sweeteners, an amount about 10 wt % or less of flavouring agents and optionally from about 1% to about 10% w/w of film coating/taste-masking substance.

According to another aspects, the pharmaceutical composition is prepared by a process comprising the steps of—preparing a blend of imatinib or a pharmaceutically acceptable salt thereof with fillers/diluents; mixing said blend with a one or more pharmaceutically acceptable excipients specifically super-disintegrants; subsequently lubricating the blend and at last either directly compressing the lubricated blend into tablets or filled into sachet dosage form.

A second aspect of the present invention provides a process for the preparation of a pharmaceutical composition of the present invention, wherein the process comprises the steps of: preparing a dry mixture of imatinib or a pharmaceutically acceptable salt thereof and fillers/diluents; blending said dry mixture with one or more pharmaceutical excipients specifically super-disintegrants; further solvent is slowly sprayed onto the powder for the granulation purpose; blending the obtained granules with extragranular excipients and lubricating the blend; At last compressing/filling the blend obtained to form a composition and optionally coating the said composition.

A third aspect of the present invention provides a process for the preparation of the pharmaceutical composition of the present invention, wherein the process comprises the steps of: blending imatinib or a pharmaceutically acceptable salt thereof, one or more fillers, binders, and super-disintegrants, and one or more pharmaceutical excipients; compacting the blend to obtain granules or flakes; further blending with a one or more pharmaceutically acceptable excipients specifically super-disintegrants; subsequently lubricating the granules/flakes using the additional lubricants; and compressing the lubricated granules into tablets or filling into sachets.

A fourth aspect of the present invention provides a process for the preparation of a pharmaceutical composition of the present invention, wherein the process comprises the steps of: blending imatinib or a pharmaceutically acceptable salt thereof, polymers and one or more pharmaceutical excipients in high shear mixer to obtain granules; loading the granules obtained in into a hot melt extruder to form a pellets in the form of extrudates; milling the extrudates and adding one or more fillers, disintegrants, and lubricants; and compressing the granules into tablets or filling into sachets.

A fifth aspect of the present invention provides a process for the preparation of a pharmaceutical composition wherein the process comprising the steps of preparing a drug containing core particles by granulating/blending the drug and optionally one or more pharmaceutically acceptable excipients; taste-masking core particles by solvent coacervation or fluid-bed coating with a water-insoluble polymer or with a mixture of water-insoluble/water-soluble polymers; blending the taste-masked particles with one or more flavouring agents, sweeteners, additional super-disintegrants; compressing the above blend into tablets or filling into the sachets.

Examples of film-forming agents include, but are not limited to, cellulose derivatives such as methylcellulose, hydroxymethyl cellulose, hydroxyethyl cellulose, hydroxypropyl cellulose, hydroxymethyl ethylcellulose, hydroxypropyl methylcellulose, sodium carboxymethyl cellulose, and ethyl cellulose; waxes; fat substances; or mixtures thereof. Alternatively, commercially available coating compositions comprising film forming polymers marketed under various trade names, such as Opadry®, may be used for coating.

Examples of solvents used for preparing the coating solution as well as granulating solution are selected from methyl alcohol, ethyl alcohol, isopropyl alcohol, n-butyl alcohol, acetone, acetonitrile, chloroform, methylene chloride, water, or mixtures thereof.

According to another embodiment, the pharmaceutical composition of the present invention exhibits bioequivalent plasma profile in comparison to marketed pharmaceutical composition of imatinib, GLEEVAC®.

In yet another embodiment of the present invention, the pharmaceutical composition remains stable for longer period of time in different thermo-hygrostats 25° C./60%+5% RH, 30° C./65%+5% RH, and 40° C./75%+5% RH as per ICH guidelines.

The pharmaceutical composition of the present invention can be used in the treatment of chronic myeloid leukemia (CML), Ph+ acute lymphoblastic leukemia, myelodysplastic/myeloproliferative diseases (MDS/MPD), aggressive systemic mastocytosis (ASM), hypereosinophilic syndrome (HES) and/or chronic eosinophilic leukemia (CEL), dermatofibrosarcoma protuberans (DFSP), and gastrointestinal stromal tumors (GIST).

The present invention is illustrated below by reference to the following examples. However, one skilled in the art will appreciate that the specific methods and results discussed are merely illustrative of the invention, and not to be construed as limiting the invention, as many variations thereof are possible without departing from the spirit and scope of the invention.

EXAMPLES

I. Oral Disintegrating Tablets (ODT)

Examples 1 and 2

TABLE 1

| Composition | Example 1 mg/dose | Example 2 mg/dose |
| --- | --- | --- |
| Imatinib | 100.00 | 400.00 |
| Mannitol (Parteck M100) | 179.50 | 284.00 |
| Crospovidone (Polyplasdone XL) | 52.00 | 75.00 |
| Colloidal Silicon Dioxide | 3.50 | 8.00 |
| Sucralose | 1.50 | 3.50 |
| Cherry Flavor (Spray Dried Natural Type) | 1.50 | 3.50 |
| Talc | 7.00 | 16.00 |
| Magnesium Stearate | 5.00 | 10.00 |
| Total | 350.00 | 800.00 |

Procedure:

1) In a high shear mixer, about half of the required quantity of mannitol (sift using screen #25) is added, followed by imatinib (sift using screen #25) and the remaining mannitol and mixed for about 5 minutes.

2) To the blend from step 1, crospovidone, colloidal silicon dioxide, sucralose, cherry flavor and talc (sift excipients using screen #25) are added and mixed for 5 minutes to achieve a uniform blend.

3) The blend from step 2 is transferred to V-blender and magnesium stearate (sift using screen #30) is added and blended for about 3 minutes.

4) The lubricated blend from step 3 is then compressed into tablets using tablet press.

Examples 3 and 4

TABLE 2

| Composition | Example 3 mg/dose | Example 4 mg/dose |
| --- | --- | --- |
| Wet Granulation | | |
| Imatinib Mesylate | 478.00** | 478.00** |
| Lactose | 50.00 | 75.00 |
| Crospovidone (Polyplasdone XL 10) | 36.00 | 36.00 |
| Povidone (Kollidon 30 LP) | 45.00 | 45.00 |
| Isopropyl Alcohol*** | NA | NA |
| Final Blending | | |
| Mannitol | 200.00 | 200.00 |
| Crospovidone (Polyplasdone XL 10) | 54.00 | 54.00 |
| Colloidal Silicon Dioxide (Aerosil 200) | 9.00 | 9.00 |
| Sucralose | 4.50 | 4.50 |
| Cherry Flavor (Spray Dried Natural Type) | 4.50 | 4.50 |
| Magnesium Stearate | 9.00 | 9.00 |
| Total | 890.00 | 915.00 |

**478.0 mg of imatinib Mesylate is equivalent to 400.0 mg of imatinib base
***Removed during processing Procedure:
1) In a high shear mixer, lactose, crospovidone (sift excipients using screen #25) is added, followed by imatinib mesylate (sift using screen #25) and mixed for about 2 minutes to achieve a uniform blend.
2) While the blend from step 1 is still mixing for additional 3 minutes, the binder solution (povidone dissolved in isopropyl alcohol) is slowly sprayed onto the powder mix until granulation end point is reached.
3) The wet granules are passed through comil and dried using fluid bed dryer.
4) The dried granules from step 3 are passed through fitz mill with the required screen size.
5) Dried milled granules are taken in a V-blender and the remaining mannitol, crospovidone, colloidal silicon dioxide, sucralose and cherry flavor (sift excipients using screen #25) are added and mixed for 5 minutes to achieve a uniform blend.
6) To the blend from step 5, magnesium stearate (sift using screen #30) is added and blended for about 3 minutes.
7) The lubricated blend from step 6 is then compressed into tablets using tablet press.
8) Tablets containing 100 mg equivalent Imatinib can be compressed on dose proportional basis.

Examples 5 and 6

TABLE 3

| Composition | Example 5 mg/dose | Example 6 mg/dose |
| --- | --- | --- |
| Granulation-Fluid bed processor | | |
| Imatinib Mesylate | 478.00** | 478.00** |
| Eudragit E | 150.00 | 200.00 |
| Lactose | 36.00 | 36.00 |
| Povidone (Kollidon 30 LP) | 45.00 | 45.00 |
| Mixture of Isopropyl Alcohol and acetone *** | NA | NA |
| Final Blending | | |
| Mannitol | 50.00 | 100.00 |
| Crospovidone (Polyplasdone XL 10) | 72.00 | 54.00 |

TABLE 3-continued

| Composition | Example 5 mg/dose | Example 6 mg/dose |
| --- | --- | --- |
| Colloidal Silicon Dioxide (Aerosil 200) | 9.00 | 9.00 |
| Sucralose | 3.50 | 3.50 |
| Cherry Flavor (Spray Dried Natural Type) | 3.50 | 3.50 |
| Magnesium Stearate | 9.00 | 9.00 |
| Total | 855.00 | 938.00 |

**478.0 mg of imatinib Mesylate is equivalent to 400.0 mg of imatinib base
*** Removed during processing Procedure:
1) In a fluid bed processor, lactose, povidone, imatinib mesylate (sift excipients using screen #25) are added and fluidized for about 5 minutes to achieve a uniform blend.
2) While the blend from step 1 is still mixing for additional 3 minutes, the polymer solution (Eudragit E dissolved in mixture of acetone and isopropyl alcohol) is slowly sprayed onto the fluidized powder blend until granulation end point is reached. The formed granules are dried in fluid bed processor following coating process at 40° C. for 10 min.
3) The dried granules are sifted from appropriate sieve.
4) Dried milled granules are taken in a V-blender and the remaining mannitol, crospovidone, colloidal silicon dioxide, sucralose and cherry flavor (sift excipients using screen #25) are added and mixed for 5 minutes to achieve a uniform blend.
5) To the blend from step 5, magnesium stearate (sift using screen #30) is added and blended for about 3 minutes.
7) The lubricated blend from step 6 is then compressed into tablets using tablet press.

Examples 7 and 8

TABLE 4

| Composition | Example 7 mg/dose | Example 8 mg/dose |
| --- | --- | --- |
| Hot Melt Extrusion | | |
| Imatinib | 100.00 | 400.00 |
| EUDRAGIT® E PO | 50.00 | 200.00 |
| Crospovidone (Polyplasdone XL) | 24.00 | 48.00 |
| Final Blending | | |
| Mannitol (Parteck M100) | 147.00 | 113.00 |
| Crospovidone (Polyplasdone XL) | 20.00 | 20.00 |
| Sucralose | 1.50 | 3.50 |
| Cherry Flavor (Spray Dried Natural Type) | 1.50 | 3.50 |
| Magnesium Stearate | 5.00 | 10.00 |
| Total | 350.00 | 800.00 |

Procedure:
1) In a high shear mixer, Eudragit® E PO, crospovidone, (sift excipients using screen #25) are added, followed by imatinib (sift using screen #25) and mixed for about 5 minutes and collected.
2) The blend is passed through a hot melt extruder, which is preset at a temperature nearly 10° C. higher than melting point of Eudragit EPO. The extrudate strands are milled using a comill with required screen size.
3) The resultant granules from step 2 are taken in a high shear mixer and mannitol, crospovidone, sucralose (sift excipients using screen #25) and cherry flavor are added and mixed for 5 minutes to achieve a uniform blend.
4) The blend from step 3 is transferred to V-blender and magnesium stearate (sift using screen #30) is added and blended for about 3 minutes.
5) The lubricated blend from step 4 is then compressed into tablets using tablet press.

II. Dispersible Tablets of Imatinib

Example 9 and 10

TABLE 5

| Composition | Example 9 mg/dose | Example 10 mg/dose |
|---|---|---|
| Wet granulation | | |
| Imatinib | 400.00 | 400.00 |
| Eudragit E | 100.00 | 150.00 |
| Lactose | 100.00 | 100.00 |
| Mixture of isopropyl alcohol and acetone** | NA | NA |
| Final Blending | | |
| Maltodextrin | 150.00 | 100.00 |
| Hydroxyethyl cellulose | 75.00 | 75.00 |
| Crospovidone | 18.00 | 18.00 |
| Sucralose | 3.50 | 3.00 |
| Flavor | 3.00 | 3.00 |
| Sodium edetate/benzoate | 1.50 | 1.00 |
| Magnesium Stearate | 9.00 | 9.00 |
| Total | 860.00 | 859.00 |

Procedure:
1) In a fluid bed processor, lactose and imatinib (sift excipients using screen #25) are added and fluidized for about 5 minutes to achieve a uniform blend.
2) While the blend from step 1 is still mixing for additional 3 minutes, the polymer solution (Eudragit E dissolved in mixture of acetone and isopropyl alcohol) is slowly sprayed onto the fluidized powder blend until granulation end point is reached. The formed granules are dried in fluid bed processor following coating process at 40° C. for 10 min.
3) The dried granules are sifted from appropriate sieve.
4) Dried milled granules are taken in a V-blender and maltodextrin, crospovidone, hydroxyethyl cellulose, sucralose, flavour and sodium benzoate (sift excipients using screen #25) are added and mixed for 5 minutes to achieve a uniform blend.
5) To the blend from step 4, magnesium stearate (sift using screen #30) is added and blended for about 3 minutes.
6) The lubricated blend from step 5 is then compressed into tablets using tablet press.
7) The lower strength of imatinib can be compressed on dose proportional basis with composition of Example 9 and 10.

III. Sachet/Granules for Dispersion Formulation of Imatinib

Example 11 and 12

TABLE 5

| Composition | Example 11 mg/dose | Example 12 mg/dose |
|---|---|---|
| Wet granulation | | |
| Imatinib | 400.00 | 400.00 |
| Eudragit E | 100.00 | 150.00 |
| Lactose | 100.00 | 100.00 |
| Mixture of isopropyl alcohol and acetone** | NA | NA |
| Final Blending | | |
| Glucose | 150.00 | 100.00 |
| Hydroxypropyl cellulose | 75.00 | 75.00 |
| Crospovidone | 18.00 | 18.00 |
| Sucralose | 3.50 | 3.00 |
| Flavor | 3.50 | 3.00 |
| Total | 850.00 | 849.00 |

Procedure:
1) In a fluid bed processor, lactose and imatinib (sift excipients using screen #25) are added and fluidized for about 5 minutes to achieve a uniform blend.
2) While the blend from step 1 is still mixing for additional 3 minutes, the polymer solution (Eudragit E dissolved in mixture of acetone and isopropyl alcohol) is slowly sprayed onto the fluidized powder blend until granulation end point is reached. The formed granules are dried in fluid bed processor following coating process at 40° C. for 10 min.
3) The dried granules are sifted from appropriate sieve.
4) Dried milled granules are taken in a V-blender and glucose, crospovidone, hydroxypropyl cellulose, sucralose and flavour (sift excipients using screen #25) are added and mixed for 5 minutes to achieve a uniform blend.
5) The blend from step 4 is then filled into suitable sachet packaging under controlled condition.
6) The lower strength of imatinib can be compressed on dose proportional basis with composition of Example 11 and 12.

The invention claimed is:
1. A stable oral pharmaceutical composition comprising imatinib, or a pharmaceutically acceptable salt thereof, and one or more pharmaceutically acceptable excipients selected from the group consisting of diluents, super-disintegrants, binders, lubricants, glidants, sweeteners, flavoring agents, coating agents, taste-masking agents, solvents, and mixtures thereof,
   wherein the composition is in the form of orally disintegrating or dispersible tablet,
   wherein the super-disintegrant is selected from the group consisting of crospovidone, povidone, sodium starch glycolate, croscarmellose sodium, a low-substituted hydroxypropylcellulose, cross-linked alginic acid, soy polysaccharides, ion-exchange resins, calcium silicate, and mixtures thereof,
   wherein the imatinib, or the pharmaceutically acceptable salt thereof, is present in an amount of from about 1 to about 80 wt %, based on the total weight of the composition, and wherein the composition disintegrates or disperses in purified water in about 60 seconds or less, measured using USP basket method.

2. The pharmaceutical composition according to claim 1, wherein the imatinib, or the pharmaceutically acceptable salt thereof, is present in an amount of from about 30 to about 80 wt %, based on the total weight of the composition.

3. The pharmaceutical composition according to claim 1, comprising a super-disintegrant, wherein the super-disintegrant is present in an amount of from about 1 to about 30 wt %, based on the total weight of the composition.

4. The pharmaceutical composition according to claim 1, comprising a diluent, wherein the diluent is selected from the group consisting of lactose, microcrystalline cellulose, starch, pre-gelatinized starch, calcium phosphate, calcium sulfate, calcium carbonate, mannitol, sorbitol, xylitol, sucrose, maltose, fructose, dextrose, maltodextrin, dextrates, dextrin, and mixtures thereof.

5. The pharmaceutical composition according to claim 1, comprising a diluent, wherein the diluent is present in an amount of from about 1 to about 80 wt %, based on the total weight of the composition.

6. The pharmaceutical composition according to claim 1, comprising a binder, wherein the binder is selected from the group consisting of starches, natural and synthetic gums, cellulose derivatives, gelatin, povidone, copovidone, polyethylene glycol, waxes, sodium alginate, alcohols, water, and mixtures thereof.

7. The pharmaceutical composition according to claim 1, comprising a binder, wherein the binder is present in an amount of from about 0.01 to about 20 wt %, based on the total weight of the composition.

8. The pharmaceutical composition according to claim 1, comprising a lubricant, wherein the lubricant is selected from the group consisting of calcium stearate, glyceryl monostearate, glyceryl palmitostearate, hydrogenated castor oil, hydrogenated vegetable oil, light mineral oil, magnesium stearate, mineral oil, polyethylene glycol, stearic acid, zinc stearate, sodium stearyl fumarate, and mixtures thereof.

9. The pharmaceutical composition according to claim 1, comprising a lubricant, wherein the lubricant is present in an amount of from about 0.1 to about 10 wt %, based on the total weight of the composition.

10. The pharmaceutical composition according to claim 1, comprising a glidant, wherein the glidant is selected from the group consisting of starches, talc, lactose, stearates, dibasic calcium phosphate, magnesium carbonate, magnesium oxide, calcium silicate, colloidal silicon dioxide, and mixtures thereof.

11. The pharmaceutical composition according to claim 1, comprising a glidant, wherein the glidant is present in an amount of from about 0.1 to about 20 wt %, based on the total weight of the composition.

12. The pharmaceutical composition according to claim 1, comprising a sweetener, wherein the sweetener is selected from the group consisting of alitame, acesulfame potassium, aspartame, D-tryptophan, dextrose, erythritol, fructose, galactose, glycerol, glycyrrhizin, glucose, isomalt, xylitol, xylose, lactitol, lactose, levulose, maltitol, maltodextrin, maltol, maltose, corn syrup, neohesperidin dihydrochalcone, neotame, sodium saccharin, cyclamate, sorbitol, sucralose, sucrose, tagatose, taumatin, trehalose, and mixtures thereof.

13. The pharmaceutical composition according to claim 1, comprising a sweetener, wherein the sweetener is present in an amount of about 25 wt % or less, based on the total weight of the composition.

14. The pharmaceutical composition according to claim 1, comprising a flavoring agent, wherein the flavoring agent is selected from the group consisting of anethole, acetic acid, ascorbic acid, phosphoric acid, fumaric acid, lactic acid, lemon, linalool, malic acid, menthol, eucalyptol, orange, citric acid, cinnamon, tartaric acid, thymol, vanilla, strawberry, cherry flavor (spray dried natural type), chocolate aroma, peppermint aroma, and mixtures thereof.

15. The pharmaceutical composition according to claim 1, comprising a flavoring agent, wherein the flavoring agent is present in an amount of about 10 wt % or less, based on the total weight of the composition.

16. The pharmaceutical composition according to claim 1, comprising from about 1% to about 80% w/w of imatinib, or the pharmaceutically acceptable salt thereof, from about 1% to about 80% w/w of diluents, from about 0% to about 20% w/w of binders, from about 1% to about 30% w/w of super-disintegrants, from about 0.1% to about 10% w/w of lubricants, from about 0% to about 20% w/w of glidants, about 25% w/w or less of sweeteners, and about 10% w/w or less of flavoring agents.

17. The pharmaceutical composition according to claim 1, comprising from about 40% to about 80% w/w of imatinib, or the pharmaceutically acceptable salt thereof, from about 5% to about 20% w/w of diluents, from about 0.5% to about 5% w/w of binders, from about 1% to about 30% w/w of super-disintegrants, from about 0.1% to about 5% w/w of lubricants, from about 0.1% to about 5% w/w of glidants, from about 0.1% to about 2% w/w of sweeteners, and from about 0.1% to about 1% w/w of flavoring agents.

18. The pharmaceutical composition according to claim 1, wherein the composition is prepared by a process comprising:
 a) blending imatinib, or a pharmaceutically acceptable salt thereof, with one or more pharmaceutically acceptable fillers, binders, and super-disintegrants to obtain a uniform blend;
 b) compacting the uniform blend from Step a) to obtain granules or flakes;
 c) blending the granules from Step b) with one or more pharmaceutically acceptable super-disintegrants;
 d) lubricating the blend from Step c) with one or more pharmaceutically acceptable lubricants to obtain a lubricated blend; and
 e) compressing the lubricated blend from Step d) into tablets.

19. The pharmaceutical composition according to claim 1, wherein the composition disintegrates or disperses in purified water in about 40 seconds or less, measured using USP basket method.

20. The pharmaceutical composition according to claim 19, wherein the composition disintegrates or disperses in purified water in about 30 seconds or less, measured using USP basket method.

* * * * *